United States Patent [19]

Winchell et al.

[11] Patent Number: 5,033,714
[45] Date of Patent: Jul. 23, 1991

[54] SYSTEMS HAVING FIXED AND VARIABLE FLOW RATE CONTROL MECHANISMS

[75] Inventors: David A. Winchell, Spring Grove; Richard J. Mitchell, Lindenhurst, both of Ill.

[73] Assignee: Baxter International Inc., Deerfield, Ill.

[21] Appl. No.: 517,917

[22] Filed: Jun. 4, 1990

Related U.S. Application Data

[60] Division of Ser. No. 449,232, Dec. 6, 1989, Pat. No. 5,014,750, which is a continuation of Ser. No. 167,822, Mar. 14, 1988, abandoned.

[51] Int. Cl.$^5$ .......................... F16K 3/32; F16K 47/04; F15D 1/14
[52] U.S. Cl. .................... 251/127; 251/208; 251/368; 138/42; 138/43; 604/246
[58] Field of Search ............ 251/127, 7, 121, 208; 138/42, 43

[56] References Cited

U.S. PATENT DOCUMENTS

| | | |
|---|---|---|
| 692,145 | 12/1968 | Cobb, Jr. . |
| 1,964,300 | 6/1934 | Perry et al. . |
| 2,236,084 | 3/1941 | Brown . |
| 2,289,905 | 7/1942 | Dasher . |
| 2,323,115 | 6/1943 | Bryant . |
| 2,376,022 | 5/1945 | Wolcott . |
| 2,506,179 | 5/1950 | Taplin . |
| 2,509,456 | 5/1950 | Saballus . |
| 2,511,733 | 6/1950 | Morrison . |
| 2,519,448 | 8/1950 | Fairchild . |
| 3,213,333 | 10/1965 | Mikina et al. . |
| 3,233,457 | 2/1966 | Martinez . |
| 3,298,367 | 1/1967 | Bergman . |
| 3,378,023 | 4/1968 | Beeken . |
| 3,398,860 | 8/1968 | Battig . |
| 3,470,915 | 10/1969 | Bitzer . |
| 3,532,126 | 10/1970 | Booth . |
| 3,532,127 | 10/1970 | Vogelsang et al. . |
| 3,587,313 | 6/1971 | Smith ................ 604/246 X |
| 3,690,318 | 9/1972 | Gorsuch . |
| 3,785,378 | 1/1974 | Stewart . |
| 3,841,354 | 10/1974 | McDonnell . |
| 3,877,428 | 4/1975 | Seagle et al. . |
| 3,882,892 | 5/1975 | Menzel . |
| 3,921,911 | 11/1975 | Bassous ............... 239/DIG. 19 |
| 3,998,427 | 12/1976 | Bentley . |
| 4,011,893 | 3/1977 | Bentley . |
| 4,079,737 | 3/1978 | Miller . |
| 4,096,879 | 6/1978 | Serur et al. . |
| 4,209,133 | 6/1980 | Mehoudar . |
| 4,275,767 | 6/1981 | Westfall ............... 138/43 X |
| 4,298,000 | 11/1981 | Thill et al. . |
| 4,300,596 | 11/1981 | Burke . |
| 4,375,813 | 3/1983 | Hessel . |
| 4,509,946 | 4/1985 | McFarlane . |
| 4,518,011 | 5/1985 | Stoll . |
| 4,527,595 | 7/1985 | Jorgensen et al. . |
| 4,534,757 | 8/1985 | Geller ................ 604/246 X |
| 4,537,680 | 8/1985 | Barth ................. 210/316 |
| 4,552,178 | 11/1985 | Olsson . |
| 4,581,624 | 4/1986 | O'Connor . |
| 4,626,244 | 12/1986 | Reinicke ............. 128/DIG. 12 X |
| 4,634,434 | 1/1987 | Marino, Jr. et al. . |
| 4,715,852 | 12/1987 | Reinicke et al. . |
| 4,756,508 | 7/1988 | Giachino et al. ........ 251/368 X |
| 4,822,344 | 4/1989 | O'Boyle . |

Primary Examiner—Arnold Rosenthal
Attorney, Agent, or Firm—Paul E. Schaafsma; Amy L. H. Rockwell; Paul C. Flattery

[57] ABSTRACT

The invention provides a flow control system well suited for use in intravenous fluid delivery systems comprising a flow restrictor wafer having one or more flow limiting flow restrictor paths formed thereon. The system provides fixed flow rate control. The system also provides means for selectively orienting at least two flow restrictor paths relative to the main fluid passage to varying the flow rate.

7 Claims, 6 Drawing Sheets

SYSTEMS HAVING FIXED AND VARIABLE FLOW RATE CONTROL MECHANISMS

This is a division of application Ser. No. 07/449,232, filed Dec. 6, 1989, now U.S. Pat. No. 5,014,750 which was a continuation of application Ser. No. 07/167,822, filed Mar. 14, 1988 now abandoned.

FIELD OF THE INVENTION

The invention generally relates to systems and methods for controlling the flow rates of fluids. More particularly, the invention relates to the maintenance of precise and stable fluid flow rates in medical fluid delivery systems.

BACKGROUND OF THE INVENTION

In many fluid delivery systems, it is important to be able to carefully control the fluid flow rates. With respect to systems intended to be used in the intravenous administration of fluids, the precise control of fluid flow rates is usually a crucial part of the therapy being provided to the patient. In the medical field, then, accuracy is an important feature of a flow control system. Furthermore, the intravenous administration of fluids at uncontrolled high fluid flow rates can be harmful to the patient.

Another desirable feature of a flow control system is consistency over time. In the medical field, it is impractical to expect a medical attendant to be present to monitor the fluid flow rate during the entire treatment session. A flow rate control system must thereby be capable of maintaining a stable flow rate while unattended for relatively long periods of time.

Also in the medical field, as well as other environments, yet another desirable feature for a flow control system is simplicity to avoid operator error, which is more likely as the complexity of a device increases. The simplicity of a flow control system also has a bearing upon the overall cost of the system, which of course is to be minimized to the fullest extent possible without detracting from the quality of performance.

Many conventional intravenous fluid administration sets are provided with manual clamping devices, such as roller clamps, which provide a means for the operator to manually control the fluid flow rates. Roller clamps have long served well for this purpose. However, as medical treatments become more sophisticated and more precise, so too should the apparatus which administer these treatments. For example, since roller clamps are virtually infinitely variable between a fully open and a fully closed position, the operator must take time to carefully adjust the clamp to achieve the rate of flow desired. Often, a desired flow rate cannot be achieved with precision. Furthermore, the flow rate, once achieved, can vary due to the tendency of flexible tubing used in intravenous administration systems to "creep" under the compression of the clamp. The flow rate initially established at the outset of the treatment session can unexpectedly and unpredictably change during the course of treatment.

In portable drug administration systems (such as shown in PCT International Publication Number WO 861 03978, entitled Infusion Having a Distal Flow Regulator, which is assigned to the same assignee as this application), extruded glass capillary tubes are sometimes used to offer a fixed resistance to flow. However, while this control technique is relatively straightforward in its approach, it is costly to extrude a capillary tube having the desired precise flow resistance.

The need therefore still exists for cost effective systems to achieve stable and precise fluid flow rate control in a fluid administration system.

SUMMARY OF THE INVENTION

To achieve these and other objectives, the invention provides systems and apparatus for precisely controlling the rate of fluid flow in a system without reliance upon expensive or complicated control mechanisms. The invention provides the means to control fluid flow either at a predetermined single fixed rate or within a range of discrete, preselected rates.

The invention provides extremely precise and stable fluid flow rate control by the use of a small, cost efficient flow restrictor wafer or chip on which one or more integrally formed flow restrictor paths are formed. The flow restrictor paths are dimensioned to achieve a preselected resistance to fluid flow to thereby control fluid flow rates.

In a preferred embodiment, the wafer is preferably formed from a semiconductor material, such as crystalline silicon. With such material, the one or more flow restrictor paths may be formed with great precision by plasma or chemical etching techniques.

One aspect of the invention is to provide a flow restrictor wafer having at least two flow restrictor paths, each offering a different resistance to flow. In this arrangement, the invention provides the means for selectively directing the fluid through the flow restrictor paths. The flow rate can thereby be controlled with precision within the range of discrete flow rates associated with the flow restrictor paths.

In another aspect, the invention provides a secondary, or "back up", fluid flow rate control for a fluid delivery system having primary flow control means. In this arrangement, the invention provides flow protection means for limiting the maximum flow rate through the system independent of the operation of the primary control means.

Other features and advantages of the invention will become apparent upon considering the accompanying drawings, description, and claims.

DESCRIPTION OF THE PREFERRED EMBODIMENTS

Figure 1:
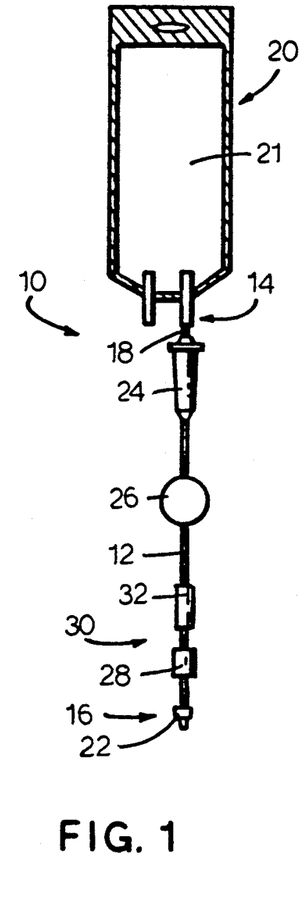
FIG. 1 is a fluid administration system having a flow rate protection device which embodies features of the invention.

A fluid delivery system 10 is shown in FIG. 1. The system includes a length of tubing 12 having an inlet end 14 and an outlet end 16. The inlet end 14 includes a connector 18 to attach the system to a source of fluid 20. The outlet end 16 includes another connector 22 to attach the system 10 to the intended fluid delivery site.

The system 10 as just described is applicable for use in a diverse number of environments. In the illustrated embodiment, the system 10 is intended for use in the medical field to delivery fluid for intravenous administration to a patient.

In this environment, the tubing 12 constitutes flexible tubing made of medical grade plastic, like polyvinyl chloride. The connector 18 comprises a conventional spike connector for attachment to the port of an intravenous solution container 21. The other connector 22 comprises a conventional luer fitment for attachment to an intravenous catheter of conventional design (not shown) which communicates with the circulatory system of the patient.

In this arrangement, the system 10 also preferably includes an inline drip chamber 24 and a filter 26.

The system 10 further includes a primary flow control device 28 located between the inlet and outlet ends 14 and 16 for the purpose of metering the flow of fluid through the tubing 12. In the illustrated embodiment, the primary flow control device 28 can take the form of a conventional roller clamp 28. By operating the roller clamp 28, the operator can open and close the fluid path through the tubing 12. The operator can also adjust the roller clamp 28 between its fully opened and fully closed position to obtain a range of desired flow rates for the fluid.

In accordance with one aspect of the invention, the system 10 includes runaway protection means 30 for limiting the maximum flow rate through the tubing 12, independent of the operation of the primary flow control device 28. The means 30 is operative, should the primary flow control device 28 be incorrectly operated, malfunction, or otherwise fail to operate properly, for automatically preventing fluid to flow through the outlet end 16 of the system 10 above a preset maximum rate. The patient is thus protected from sudden "runaway" flow rates which would be considered unsafe from a medical standpoint.

In the illustrated embodiment (see also FIGS. 2 and 3), the run-away protector means 30 takes the form of an inline fixed flow rate control member 32. In accordance with the invention, this member 32 includes a housing 34 in which a preformed flow restrictor chip or wafer 36 is encapsulated.

Figure 2:
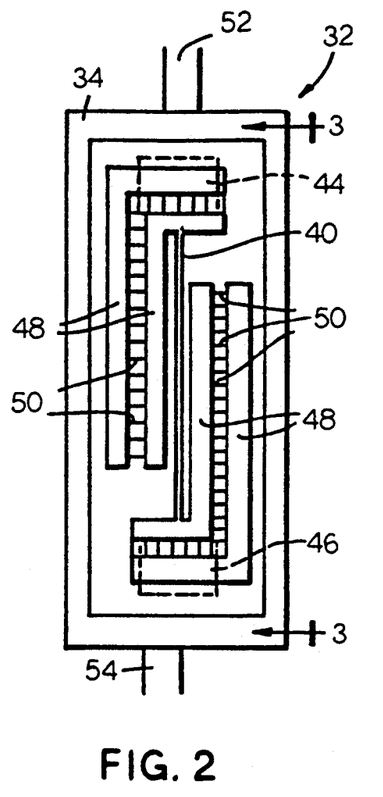
FIG. 2 is an enlarged top view of the flow rate wafer shown in FIG. 1.
Figure 3:
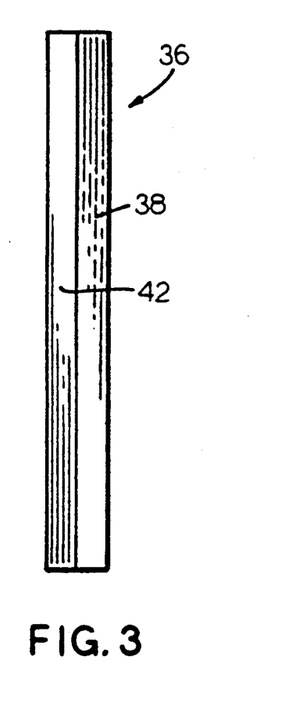
FIG. 3 is a side section view of the wafer taken generally along line 3—3 in FIG. 2.

As shown in FIGS. 2 and 3, the wafer includes a base substrate 38 into which one or more flow restrictor paths 40 are formed. These paths can be of various geometries, such as V-shaped; accurately shaped; or rectangularly shaped, depending upon the nature of the substrate and the etching technique used. In the illustrated embodiment, a single main flow restrictor path 40 is formed having a preselected discrete resistance to fluid flow. The flow restrictor path 40 is enclosed. The path 40 may be enclosed by various means, however, in the illustrated embodiment, an overlay 42 covers the base substrate 38, thereby enclosing the restrictor path 40. The wafer 36 further includes an inlet 44 and an outlet 46 in the base substrate 38 which communicate at opposite ends of the flow restrictor path 40 to thereby conduct fluid into and out of the flow restrictor path 40.

Preferably, manifold regions 48 are also preformed in the base substrate 38 at the opposite ends 44 and 46 of the flow restrictor path 40 to assure a non-restricted flow on the wafer 36.

Also in the illustrated embodiment, a plurality of flow restrictor paths 50, each smaller than the main flow restrictor path 40 are provided to filter out small particulate matter during passage across the wafer 36.

The material of the base substrate 38 can be selected among the materials on which discrete fluid flow path patterns can be formed. Such materials can be metallic, ceramic, or polymer in nature. Crystalline structures by their nature offer greater precision in the formation of flow patterns. For this reason, in the illustrated and preferred embodiment, the base substrate 38 is formed of a semiconductor material, such as crystalline silicon. In this arrangement, the main flow restrictor path 40, the smaller flow restrictor paths 50, and manifolds 48 are formed by conventional etching techniques, such as disclosed in Barth U.S. Pat. No. 4,537,680. In this arrangement, the flow restrictor paths can be formed with a precise V-shaped geometry. The overlay 42 can be glass, or it can comprise a semiconductor material like the substrate itself. The overlay 42 can be suitably bonded to the base substrate 38, for example, by using a conventional anodic bonding process.

As shown in FIG. 2, the housing 34 in which the wafer 36 is encapsulated has an inlet passage 52 communicating with the wafer inlet 44 and an outlet passage 54 communicating with the wafer outlet 46. These passages 52 and 54 are, in turn, attached to the tubing 12 of the fluid delivery system 10.

The interior cross sectional area and the length of the flow restrictor path 40 can be preselected in a precise manner to obtain the desired fixed flow rate through the wafer 36. The flow rate of fluid through a given flow restrictor path is governed by various known equations, for example the Hagen-Pouisvelle equation. This equation can be expressed as:

$$Q = \frac{A^2}{\pi 8 \mu} \left[ \frac{\Delta P}{L} - pg \sin \theta \right]$$

where
Q = volumetric flow rate
A = cross sectional area of the flow restrictor path
$\mu$ = fluid viscosity
$\Delta P$ = pressure drop through the flow restrictor path
L = restrictor path length
p = fluid density
g = gravitation acceleration
$\theta$ = orientation angle of the flow restrictor path relative to gravity In the illustrated application, gravitational effects are negligible. Thus, from the equation, it can be seen that the flow through a given flow restrictor path is controlled primarily by (1) the head height or pressure exerted on the fluid source as compared with the pressure exerted at the outlet of the system (i.e. $\Delta P$); (2) $A^2/L$ ratio; and (3) the viscosity ($\mu$) of the fluid. Of these, the critical control variable is the $A^2/L$ ratio. By use of a crystalline substrate, this ratio can be precisely controlled to achieve a precise and nonvarying flow restrictor path.

The fixed rate flow restrictor as heretofore described is applicable for use in other fluid administration systems in the medical field. For example, in FIG. 4, the restrictor is part of a portable drug infusion system 58.

Figures 4, 5, 6:
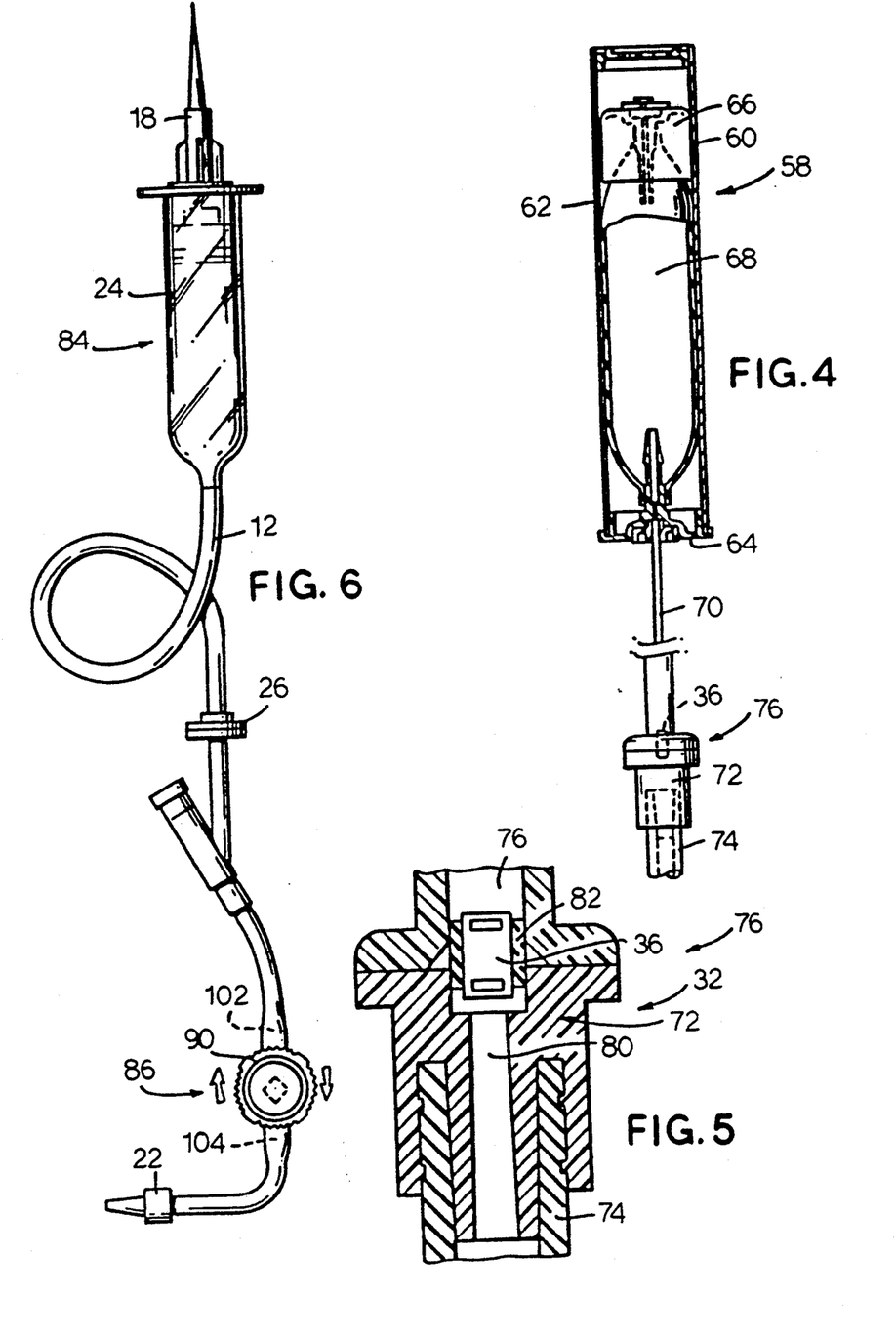
FIG. 4 is a drug infusion system having a fixed flow rate control device which embodies the features of the invention.
FIG. 5 is an enlarged sectional view of the control device shown in FIG. 4.
FIG. 6 is a fluid delivery system having a variable flow rate control device which embodies features of the invention.

The system 58 shown in FIG. 4 includes a conventional bladder-type infusor 60 of the type described in Peery et al. U.S. Pat. No. 4,386,929. This infusor 60 is intended to be carried or worn by the patient while medication is intravenously delivered at a fixed, controlled rate.

The infusor 60 includes a tubular housing 62 having an outlet end 64. A floating piston 66 is movably mounted in the housing 62. An elastomeric bladder 68 is secured to the piston 66. In use, the liquid drug or other medicament intended to be administered is conveyed into the bladder 68 by a syringe or the like. Liquid is expressed from the expanded bladder 68 through the outlet end 64. The piston 66 correspondingly moves toward the outlet end 64 of the housing 62.

Tubing 70 communicates with the interior of the bladder 68 and carries the liquid from the bladder 68 to the patient. As in FIG. 1, in use, a conventional luer fitment 72 carried at the end of the tubing 70 connects with a conventional intravenous catheter 74.

In accordance with this aspect of the invention, the system 58 includes an inline fixed flow rate control member 76 comprising a wafer 36 or chip having the same general configuration and construction (thereby being designated with the same reference number) as shown in FIG. 2. As before described, the interior diameter and length of the flow restrictor path 40 through the wafer 36 will maintain the desired flow rate of medication to the patient.

The wafer 36 can be placed in a housing 34 as shown in FIG. 2 and be located anywhere along the fluid path communicating with the interior of the bladder 68. However, in the illustrated embodiment (see FIG. 5), the wafer 36 is housed within the luer fitment 72 itself.

In this particular arrangement, the luer fitment 72 includes an inlet passage 78 communicating with the bladder 68 and an outlet passage 80 communicating with the catheter 74. A seal member 82 is located between the inlet and outlet passages 78 and 80. The wafer 36 is carried within the seal member 82 with the wafer inlet 44 communicating with the inlet passage 78 and the wafer outlet 46 communicating with the outlet passage 80. All fluid traversing the fitment 72 must thus pass through the flow restrictor path 40 of the wafer 36. The wafer 36 thus serves to regulate the flow rate of the fluid.

Yet another fluid administration system 84 is shown in FIG. 6. This system 84 shares many common elements with the system shown in FIG. 1, and these common elements share the same reference numerals.

However, as can be seen in FIG. 6, the system 84 does not include the roller clamp 28. Rather, taking the place of this element, the system 86 includes a single inline variable flow rate control member which embodies the features of the invention.

Figure 7:
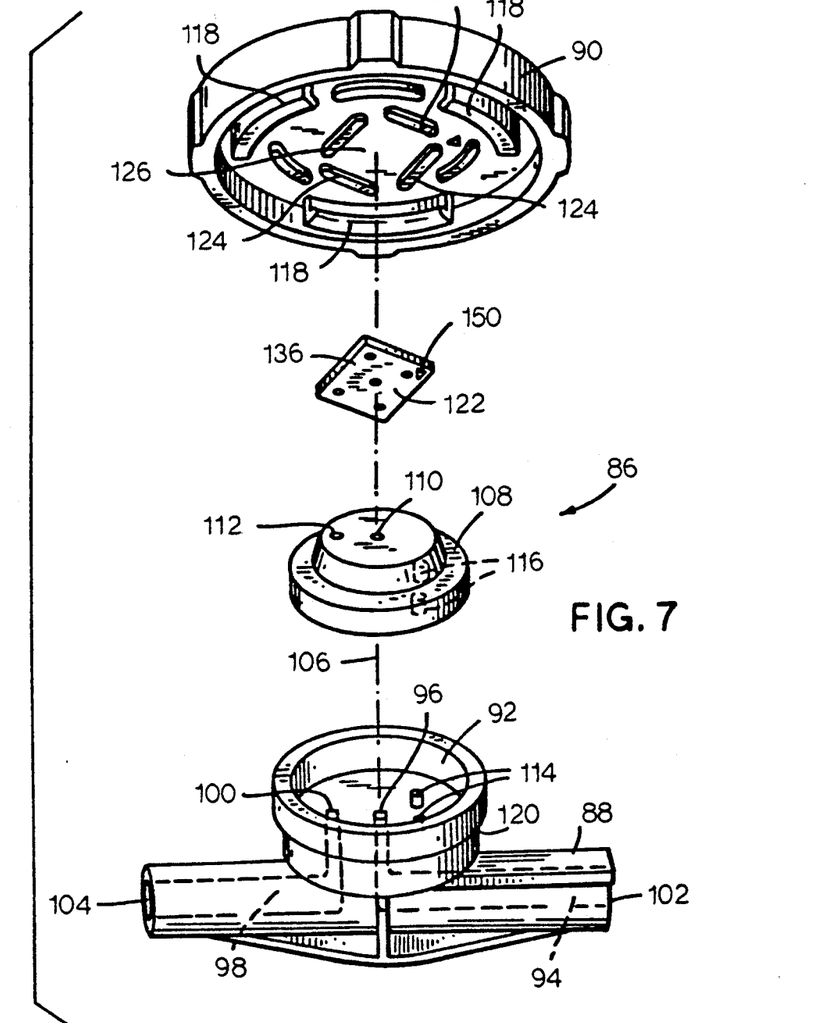
FIG. 7 is an exploded perspective view of the variable rate control device shown in FIG. 6.

As can be best seen in FIG. 7, the inline variable flow rate control member 86 includes a base member 88 and a selector member 90 which is movable carried on the base member 88. As will be described in greater detail below, movement of the selector member 90 (as shown by arrows in FIG. 6) serves to selectively vary the flow rate of fluid traversing the system 84. Movement of the selector member 90 can also serve to prevent fluid flow through the system 84 altogether.

As shown in FIG. 7, the base member 88 includes a well 92. An inlet passage 94 communicates with the well 92 via an inlet port 96. Likewise, an outlet passage 98 communicates with the well 92 via an outlet port 100. The opposite ends of the inlet and outlet passage, respectively 102 and 104, are attached inline with the fluid tubing 12 of the system 84 (see FIG. 6).

As can be seen in FIG. 7, the inlet port 96 is located generally along the centerline 106 of the well 92, which in the illustrated embodiment, is shown to be cylindrical in configuration. The outlet port 100 in this arrangement is radially spaced a selected distance away from the inlet port 96.

It should be appreciated that the position of the inlet and outlet ports 96 and 100 would be reversed, and the well 92 could assume other than a cylindrical configuration, as shown in the drawings.

An elastomeric seal member 108 occupies the well. The seal member 108 includes first and second apertures 110 and 112 which extend through the body of the member 108. The first aperture 110 registers with the inlet port 96 when the seal member 108 is properly positioned in the well 96. When thus positioned, the second aperture 112 registers with the outlet port 100.

A pair of locating pins 114 is positioned in the well 92. These pins 114 mate with a pair of locating holes 116 in the seal member 108 to align and retain the seal member 108 in the desired position in the well 92.

In the illustrated embodiment, the selector member 90 is rotatable on the base member 88 about an axis generally aligned with the centerline 106 of the well 92, i.e., axially aligned with the inlet port 96.

While the selector member 90 can be rotatably attached to the base member 88 by various means, in the illustrated embodiment (see FIG. 7), the selector member 90 is rotatably affixed to the base 88 by snap-fit engagement between a circumferential flange 118 on the selector member 90 and a mating circumferential ridge 120 on the base member 88.

A flow restrictor wafer 122 or chip is carried by the selector member 90. More particularly, projecting ridges 124 formed within the inner wall of the selector member 90 define a space 126 generally corresponding to the shape of the wafer 122. The wafer 122 is carried within this space 126, with the ridges 124 contacting the peripheral edges of the wafer 122 and preventing lateral movement thereof. The wafer 122 is thus carried for movement in common with the selector member 90.

The wafer 122 is constructed as above described and shown in FIGS. 2 and 3, with a base substrate 38 and an overlay 42. Unlike the wafers previously shown and described (and refer now to FIG. 8), the wafer 122 includes at least two independent flow restrictor paths formed in the base substrate. In the illustrated embodiment, four flow restrictor paths 128, 130, 132, 134 are formed.

Figure 8:
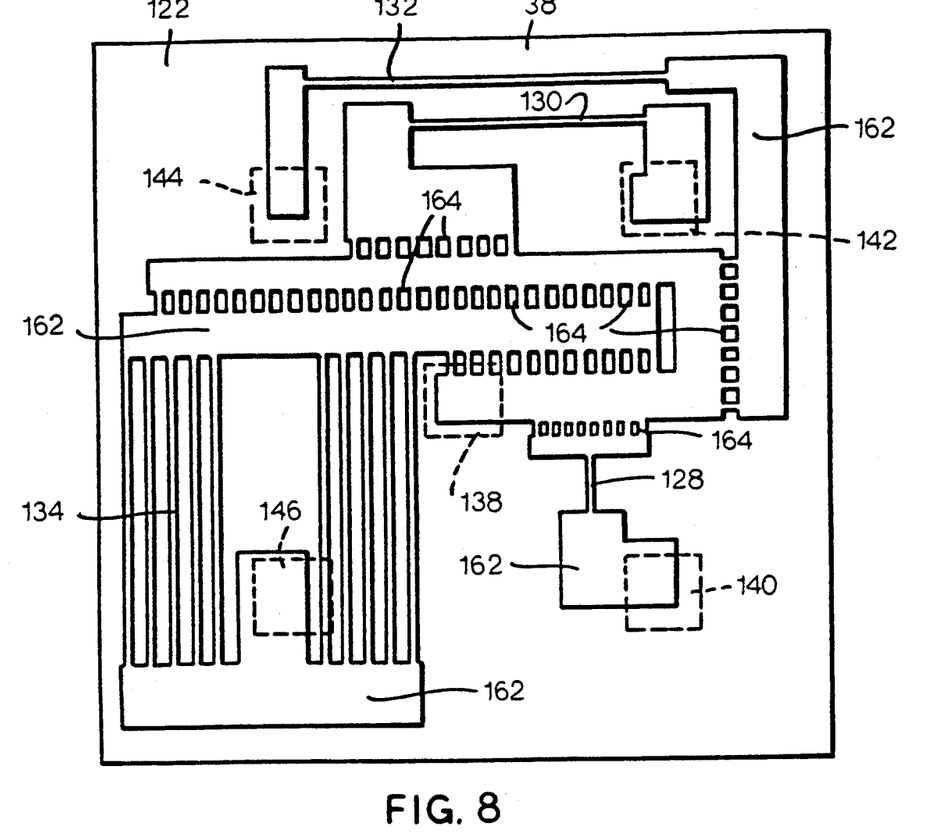
FIGS. 8 is an enlarged top view of the flow rate control wafer shown in FIG. 7.

When the selector member 90 is rotatably affixed to the base member 88, the wafer 122 is sandwiched within the space 126 between the inner wall of the selector member 90 and the seal member 108. In this orientation, the mid point 136 of the wafer 122 is generally aligned with the axis of rotation 106 of the selector member 90, and is therefore aligned with the inlet port 96 itself.

Rotation of the selector member 90 thus serves to rotate the wafer 122 about this axis 106, with the seal member 108 forming a sliding sealing surface adjacent to the wafer 122.

In this arrangement, the wafer 122 includes at its midpoint an inlet 138 (see FIG. 8). Radially spaced from the inlet 138 are at least two outlets. In the illustrated embodiment, four outlets 140, 142, 144, 146 are shown. Each outlet 140, 142, 144, and 146 is radially spaced from the inlet 138 the same distance that the outlet port 100 is spaced from the inlet port 96.

When the wafer 122 is sandwiched between the selector member 90 and the seal member 108, the inlet 138 of the wafer thus registers with the inlet port 96 of the base member 88 (via the aperture 110 in the seal member 108). Rotation of the wafer 122 in common with the selector member 90 thus serves to keep the inlet 138 of the wafer 122 in registration with the inlet port 96 of the base member 88 (via the registering aperture 110 in the seal member 108). Rotation also serves to place the various outlets 140, 142, 144, and 146 of the wafer 122 into and out of registration with the outlet port 100 of the base member 88 (via the registering aperture 112 in the seal member 108), depending upon the position of the selector member 90 within its circular path (as shown by arrows in FIG. 6).

As can be seen in FIG. 8, the first, second, third, and fourth paths 128, 130, 132, and 134 are formed in the substrate 38 of the wafer 122 between the wafer inlet 138 and, respectively, the first, second, third, and fourth wafer outlets 140, 142, 144, and 146. Each path 128, 130, 132, and 134 is formed with a preselected cross sectional area and length to provide a different resistance to flow. Fluid traversing each flow restrictor path will therefore flow at a different rate.

Figure 9:
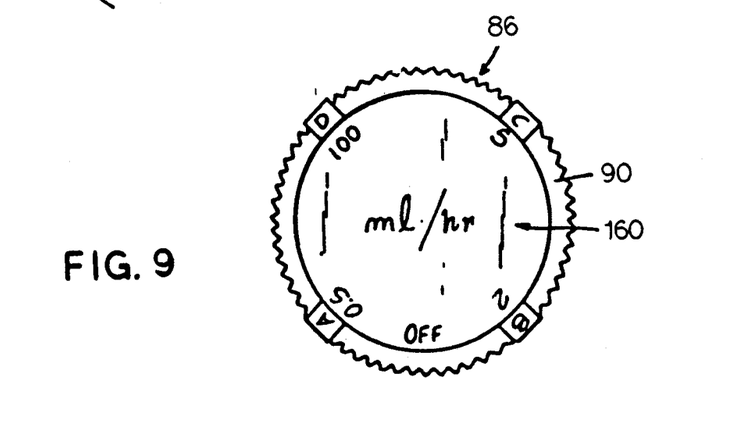
FIG. 9 is a top view of the flow rate control device shown in FIG. 6.
Figure 10A:
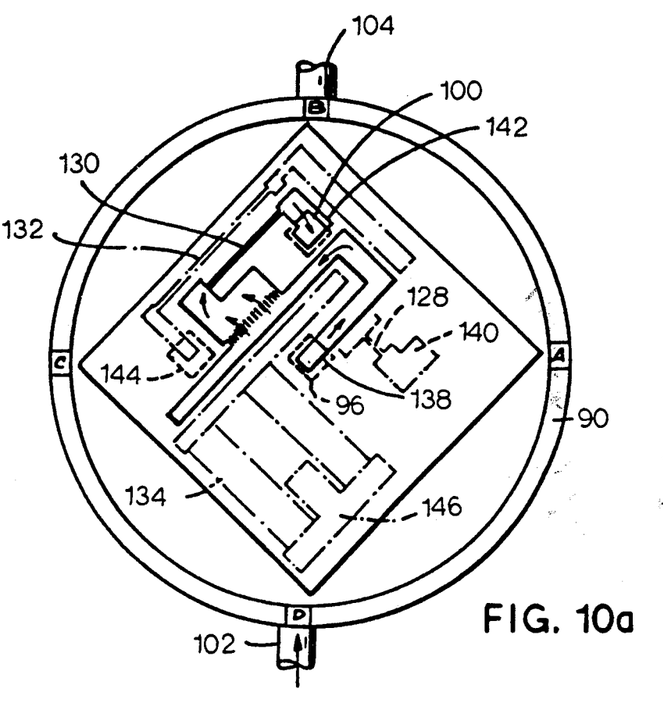
FIGS. 10a to 10d are a series of views showing the variable control features of the device shown in FIG. 6.
Figure 10B:
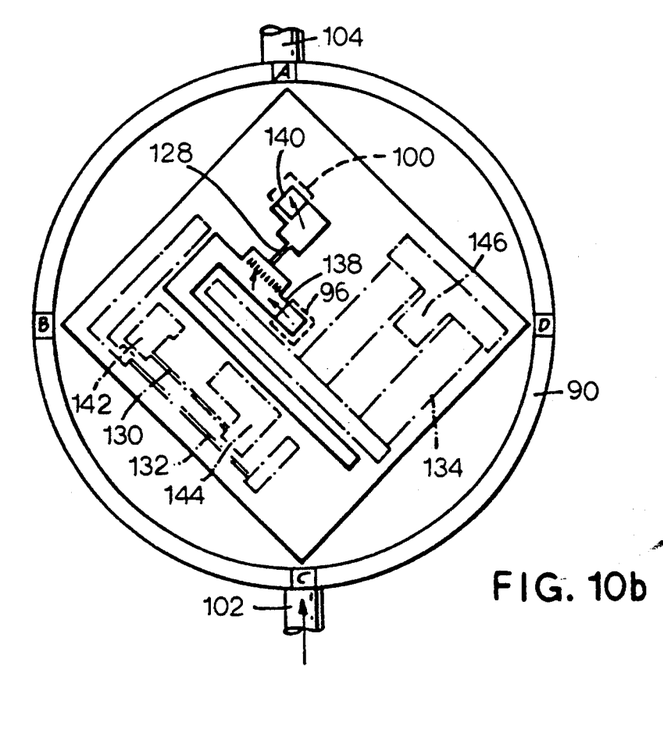
Figure 10C:
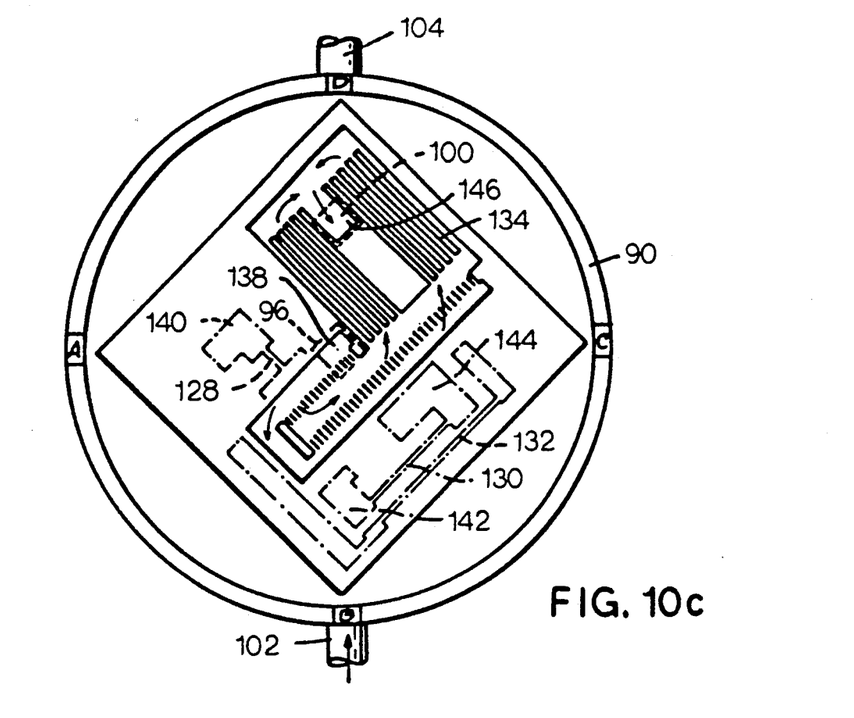
Figure 10D:
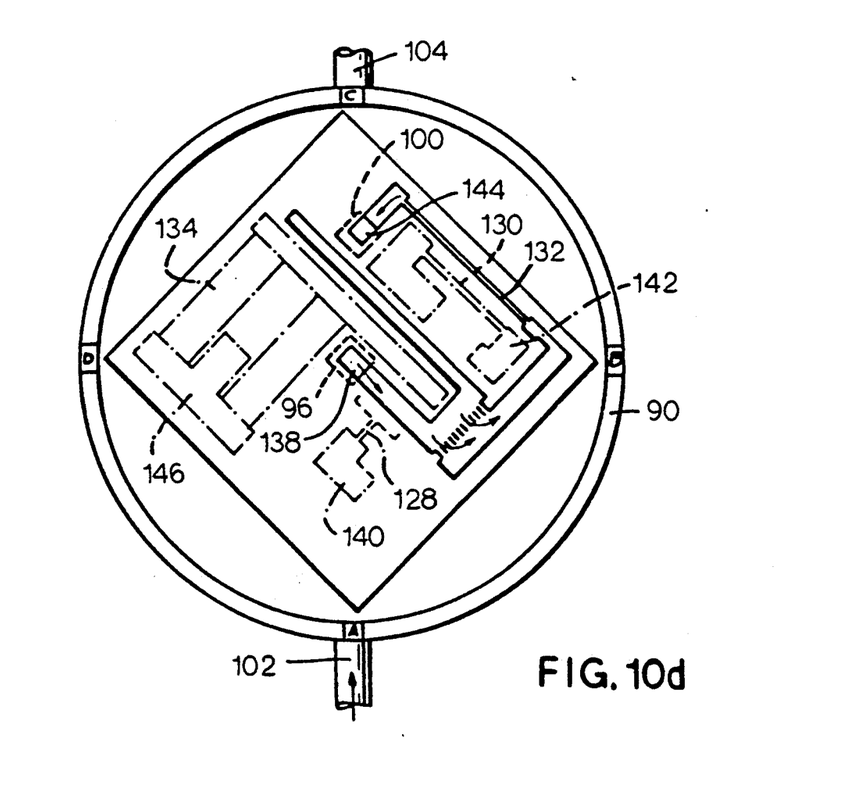

A scribe mark 148 on the inner wall of the selector member 90 (see FIG. 7) aligns with a corresponding scribe mark 150 on the wafer 122 to locate the wafer 122 in the desired orientation within the space 126. In this orientation, descriptive markings 160 on the exterior of the selector member 90 (see FIG. 9) indicate when the various wafer outlets are in or out of registration with the outlet port 100.

As shown in FIGS. 10a to 10d, the user can thus selectively orientate the wafer 122 by rotating the selector member 90 within a range of positions (described as Positions A, B, C, and D) to direct the fluid flow through the flow restrictor paths 140, 142, 144, and 146 to obtain the desired flow rate. By positioning the selector member 90 between any of these operative positions, the wafer 122 serves to block all fluid flow through the system.

Preferably, as shown in FIG. 8 fluid manifolds 162 are formed in association with each flow restrictor path. If desired, filtration areas 164 as above described can also be formed.

In the illustrated embodiment, the first flow restrictor path 128 (Position A) meters fluid flow at a rate of 0.5 mls/hr; the second flow restrictor path 130 (Position B) at 2.0 mls/hr; the third flow restrictor path 132 (Position C) at 5.0 mls/hr; and the fourth flow restrictor path 134 (Position D) at 100 mls/hr, when the system 84 is being operated under its normal operating conditions.

In the illustrated embodiment, all of the flow restrictor paths 128, 130, 132, and 134 are V-shaped, with an included angle within the V of 70½. The first path 128 has width measured at the top of the V of 22 microns and a length of 330 microns. The second path 130 has a comparable width of 48 microns and a length of 1980 microns. The third path 132 has a width of 66 microns and a length of 2760 microns. The fourth path 134 is comprised of ten (10) parallel paths each 76 microns in width and 2390 microns in length. As used in this application, the term "path" can include, as in the fourth path 134, more than a single fluid passage and can comprise a pattern of fluid passages.

The flow rates provided are discrete and precise. The user does not have to initially adjust an infinitely adjustable roller clamp to obtain a desired flow rate. Furthermore, once selected, the flow rate set by the wafer is fixed and invariable as long as the operating conditions (such as the effective head height $\Delta P$) remain constant. It is not subject to change due to "creep" in the tubing, as with a conventional roller clamp.

Figure 11:
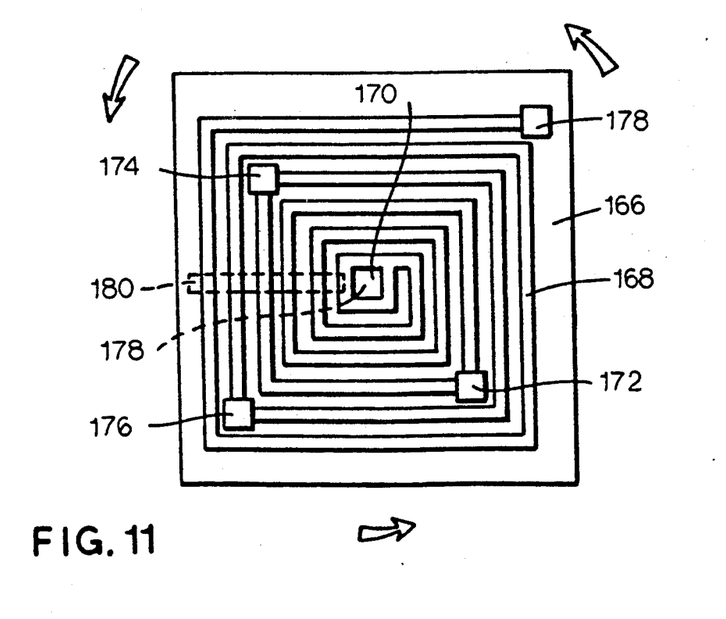
FIG. 11 is an alternate embodiment of a variable flow rate control wafer which embodies the features of the invention.

The arrangement of the flow restrictor paths upon the base substrate to achieve a range of discrete flow rates can vary from that shown in FIG. 8. A representative alternate arrangement is shown in FIG. 11. There, a wafer 166 (constructed as shown in FIGS. 2 and 3) includes a continuous concentric flow restrictor path 168 extending from a center opening 170 outwardly in the shape of a helix. Several openings 172, 174, 176, 178 are located along the path 168. Four flow restrictor paths are thereby defined, extending between opening 170 and opening 172; opening 170 and 174; opening 170 and 176; and opening 170 and 178. Each flow restrictor path has a different flow resistance due to its length and cross sectional area, thereby creating a range of discrete flow rates.

In this arrangement (as shown in FIG. 11) the center opening 170 can be aligned with an inlet port 178 located in an associated housing. An outlet port 180 can be arranged adjacent to the inlet port 178 on the housing. Rotation of the wafer 166 about the inlet port 178 will bring the outlets 172, 174, 176 and 178 into and out of registration with the outlet port 180 to achieve the variable flow rate control as described with respect to FIG. 8.

Various of the features of the invention are set forth in the following claims.

We claim:

1. A device for controlling fluid flow in a fluid path comprising
   a flow restrictor wafer including a substrate having at least two enclosed flow restrictor paths, each path presenting a different resistance to fluid flow to create at least two preselected fluid flow rates through said device,
   the flow restrictor wafer including first, second, and third openings with one of said flow restrictor paths extending between said first opening and said second opening and the other of said flow restrictor paths extending between said first opening and said third opening, and
   means for relatively choosing the desired one of said flow restrictor paths for the transport of fluid.

2. A flow control device according to claim 1 wherein said selection means includes means for selectively effecting relative movement between said flow restrictor wafer and the fluid path to direct fluid through the desired one of said flow restrictor paths.

3. A flow control device according to claim 1 and further including a housing which includes an inlet and an outlet and means for conveying fluid through said inlet into said first wafer opening, wherein said flow restrictor wafer is carried by said housing, and wherein said selection means includes means for effecting relative movement between said housing and said wafer to move each of said second and third openings selectively into and out of communication with said housing inlet.

4. A flow control device according to claim 1 wherein said substrate is formed of a crystalline material, and wherein said flow restrictor path is etched in said substrate.

5. A flow control device comprising a base member, a selector member movably carried on said base member, a flow restrictor wafer including a substrate having at least two enclosed flow restrictor paths, each path presenting a different resistance to fluid flow to create at least two preselected fluid flow rates through said device, the flow restrictor wafer including a first, second, and third openings with one of said flow restrictor paths extending between said first opening and said second opening and the other of said flow restrictor paths extending between said first opening and said third opening, and means operatively connecting said flow restrictor wafer and said selector member for selectively choosing the desired one of said flow restrictor paths for the transport of fluid in response to movement of said selector member.

6. A flow control device according to claim 5 and further including a sealing member carried by said base member, and wherein said flow restrictor wafer is carried within said housing between said sealing member and the interior of said selector member.

7. A flow control device according to claim 5 wherein said substrate is formed of a crystalline material, and wherein said flow restrictor path is etched in said substrate.

* * * * *